United States Patent
Jung

(10) Patent No.: US 10,456,210 B2
(45) Date of Patent: Oct. 29, 2019

(54) SURGICAL INSTRUMENT ORGANIZING PAD

(71) Applicant: Seonghum Jung, Seoul (KR)

(72) Inventor: Seonghum Jung, Seoul (KR)

( * ) Notice: Subject to any disclaimer, the term of this patent is extended or adjusted under 35 U.S.C. 154(b) by 0 days.

(21) Appl. No.: 16/170,109

(22) Filed: Oct. 25, 2018

(65) Prior Publication Data

US 2019/0060022 A1 Feb. 28, 2019

Related U.S. Application Data

(63) Continuation of application No. PCT/KR2017/004393, filed on Apr. 26, 2017.

(30) Foreign Application Priority Data

Apr. 26, 2016 (KR) .................. 10-2016-0050620

(51) Int. Cl.
*A61B 50/22* (2016.01)
*A61B 1/00* (2006.01)
(Continued)

(52) U.S. Cl.
CPC .......... *A61B 46/23* (2016.02); *A61B 1/00147* (2013.01); *A61B 50/20* (2016.02);
(Continued)

(58) Field of Classification Search
CPC ..... A61B 50/22; A61B 90/50; A61B 1/00147; A61B 46/23
See application file for complete search history.

(56) References Cited

U.S. PATENT DOCUMENTS

| | | | | |
|---|---|---|---|---|
| 2,903,129 | A * | 9/1959 | Anderson, III | ........ A61B 50/22 206/363 |
| 3,503,391 | A * | 3/1970 | Melges | .................. A61B 46/00 128/852 |

(Continued)

FOREIGN PATENT DOCUMENTS

| | | | | |
|---|---|---|---|---|
| DE | 29509786 U1 * | 8/1995 | ............ A61M 5/008 |
| JP | H08-072791 A | 3/1996 | |

(Continued)

OTHER PUBLICATIONS

Auction, non-slip holdable pad for vehicle, http://itempage3.auction.co.kr/detailView.aspx?ItemNo=A962472597&keyword=%b3%ed%bd%bd%b8%b3%c6%d0%b5%e5&scoredtype=2.

*Primary Examiner* — Stanton L Krycinski
(74) *Attorney, Agent, or Firm* — KORUS Patent, LLC; Seong Il Jeong

(57) ABSTRACT

A surgical instrument organizing pad according to the present invention includes: a soft pad configured such that it is fabricated in a size enabling it to be held on the body of a patient and a seating area on which a surgical instrument is seated is formed on the top surface of the center portion thereof; and partitions erected along the circumference of the seating area. The soft pad and the partitions are made of soft resin. The surgical instrument organizing pad according to the present invention are advantageous in that surgical instruments having any materials or various dimensions can be stably placed thereon, there can be prevented a phenomenon in which a surgical instrument falls because an electric cable attached to the surgical instrument is twisted or caught, and a placement structure for surgical instruments can be changed in various manners according to the convenience of a user.

5 Claims, 9 Drawing Sheets

(51) Int. Cl.
*A61B 90/50* (2016.01)
*A61B 46/23* (2016.01)
*A61B 90/00* (2016.01)
*A61B 50/20* (2016.01)
*A61B 50/30* (2016.01)

(52) U.S. Cl.
CPC .............. *A61B 50/22* (2016.02); *A61B 50/30* (2016.02); *A61B 90/00* (2016.02); *A61B 90/50* (2016.02); *A61B 2050/21* (2016.02)

(56) References Cited

U.S. PATENT DOCUMENTS

| | | | | |
|---|---|---|---|---|
| 3,654,047 | A * | 4/1972 | Berkowitz | A61B 46/23 128/852 |
| 4,051,845 | A * | 10/1977 | Collins | A61B 46/23 128/855 |
| 4,476,860 | A * | 10/1984 | Collins | A61B 46/23 128/852 |
| 4,553,538 | A * | 11/1985 | Rafelson | A47G 9/10 128/852 |
| 4,570,628 | A * | 2/1986 | Neal | A61B 46/30 128/853 |
| 4,596,245 | A * | 6/1986 | Morris | A61M 25/02 128/852 |
| 4,793,483 | A * | 12/1988 | Holmes | A61G 7/0503 206/210 |
| 4,944,311 | A * | 7/1990 | Eldridge, Jr. | A61B 46/23 128/849 |
| 5,010,899 | A * | 4/1991 | Thompson | A61B 46/23 128/849 |
| 5,036,866 | A * | 8/1991 | Eldrige, Jr. | A61B 46/23 128/849 |
| 5,046,624 | A * | 9/1991 | Murphy | A47F 7/0028 206/370 |
| 5,170,804 | A * | 12/1992 | Glassman | A61B 50/10 128/849 |
| 5,195,538 | A * | 3/1993 | Eldridge, Jr. | A61B 46/23 128/849 |
| 5,207,703 | A * | 5/1993 | Jain | A61B 17/06061 606/232 |
| 5,284,632 | A | 2/1994 | Kudla et al. | |
| 5,387,177 | A * | 2/1995 | Dunn | A61G 7/05715 128/897 |
| 5,728,047 | A * | 3/1998 | Edoga | A61B 17/02 600/102 |
| 5,762,202 | A * | 6/1998 | Atad | A61C 19/02 206/369 |
| 5,800,346 | A * | 9/1998 | Adams | A61B 17/02 600/201 |
| D456,517 | S * | 4/2002 | Kraska | D24/189 |
| 7,040,484 | B1 * | 5/2006 | Homra | A61B 50/13 206/363 |
| 7,201,747 | B2 * | 4/2007 | Edoga | A61B 17/02 606/1 |
| 8,505,748 | B2 * | 8/2013 | Jones | A61B 17/06061 206/370 |
| 8,707,961 | B1 * | 4/2014 | Kazravan | A61B 46/10 128/849 |
| 2004/0222175 | A1 * | 11/2004 | Keating | A61B 50/22 211/85.13 |
| 2006/0076254 | A1 * | 4/2006 | Corbitt, Jr. | A61B 50/22 206/370 |
| 2011/0095158 | A1 * | 4/2011 | Laker | A61B 90/57 248/346.5 |

FOREIGN PATENT DOCUMENTS

JP           5475890 B2    4/2014
KR     10-1455215 B1    11/2014

* cited by examiner

SURGICAL INSTRUMENT ORGANIZING PAD

TECHNICAL FIELD

The present invention relates to a surgical instrument organizing pad which is capable of keeping surgical instruments stably seated during surgery, and more specifically to a surgical instrument organizing pad which is capable of effectively overcoming a problem in which a surgical instrument falls or an electric cable connected to a surgical instrument is twisted, or the like.

BACKGROUND ART

Generally, various types of surgical instruments are alternately used during surgery. A nurse who hands and receives surgical instruments to and from a doctor is located beside the doctor. In order to accurately hand required surgical instruments to a doctor, communication between staff members must be accurately performed. However, a problem arises in that there are cases where communication between staff members cannot be accurately and rapidly performed in an urgent surgical situation.

Due to the above problem, there are many cases where a doctor actually puts and uses frequently-used surgical instruments in his or her surroundings rather than handing them to a nurse. In this case, the surgical instruments are usually placed on the abdomen or leg of a patient, and are then used. Since the top surface of the abdomen or leg of a patient is not a flat surface but a curved surface, there are cases where the placed surgical instruments often fall down.

Furthermore, when a heated electric cauterizer or a sharp surgical instrument is placed directly on the body of a patient or when a surgical instrument falls down to a patient during the replacement of a surgical instrument between medical staff members, there occurs an accident in which the patient is injured.

In order to overcome the above problem, there is used a rubber pad capable of fastening a surgical instrument by means of the magnetic force of a built-in magnet. In recent years, surgical instruments have not been made of iron but are increasingly made of stainless steel or titanium, and thus a problem arises in that the surgical instruments are not effectively fastened. In particular, a problem arises in that a surgical instrument having a long length or an electric surgical instrument having an electric cable cannot be stably fastened onto the rubber pad configured as described above.

PRIOR ART DOCUMENT

<Patent Document>

(Patent document 1) KR 10-1455215 B1

DISCLOSURE

Technical Problem

The present invention has been proposed to overcome the above-described problems, and an object of the present invention is to provide a surgical instrument organizing pad which enables a surgical instrument made of any material to be stably seated, which can prevent a phenomenon in which a surgical instrument falls because an electric cable attached to the surgical instrument is twisted or caught from occurring, and which enables surgical instruments having various dimensions to be stably placed thereon.

Technical Solution

In order to accomplish the above object, the present invention provides a surgical instrument organizing pad including: a soft pad configured such that it is fabricated in a size which enables it to be held on the body of a patient and a seating area on which a surgical instrument is seated is formed on the top surface of the center portion thereof; and partitions erected along the circumference of the seating area; wherein the soft pad and the partitions are made of soft resin.

Each of the partitions may include a plurality of unit plates, and each of the unit plates may be formed in an upward convex shape.

Each pair of two neighboring ones of the unit plates may be spaced apart from each other so that the electric cable of the surgical instrument can pass between the two neighboring unit plates and a space can be ensured to fasten a surgical instrument which is formed to be long and slender in accordance with endoscopic surgery corresponding to a current surgery trend.

The surgical instrument organizing pad may further include one or more detachable cases formed in a box or pocket shape having an open top and configured to be detachably attached onto both sides of the soft pad in the lengthwise direction thereof.

A plurality of mounting holes may be formed in both sides of the soft pad in the lengthwise direction thereof, and the detachable cases may be provided with mounting tools which can be inserted into the mounting holes.

Pluralities of mounting holes may be formed in both sides of the soft pad in the lengthwise direction thereof and in the detachable cases, and the surgical instrument organizing pad may further include mounting loops configured to connect the mounting holes of the soft pad and the mounting holes of the detachable cases.

The soft pad may be formed in a cross or rectangular shape on a plane, and the seating area may be formed to be inclined such that the height of the seating area increases toward both ends of the seating area in the widthwise direction thereof.

Advantageous Effects

The surgical instrument organizing pad according to the present invention are advantageous in that surgical instruments made having any materials or various dimensions can be stably placed thereon, there can be prevented a phenomenon in which a surgical instrument falls because an electric cable attached to the surgical instrument is twisted or caught, and a placement structure for surgical instruments can be changed in various manners according to the convenience of a user.

MODE FOR INVENTION

Embodiments of a surgical instrument organizing pad according to the present invention will be described in detail below with reference to the accompanying drawings.

Figure 1:
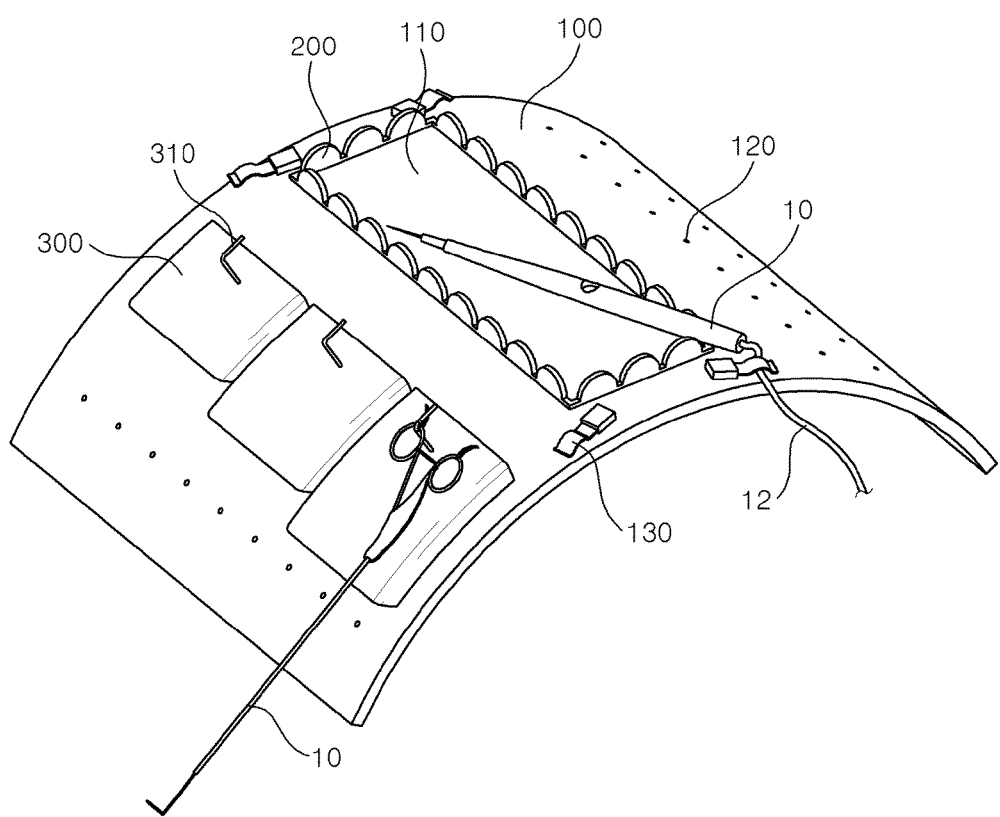
FIG. 1 is a perspective view of a surgical instrument organizing pad according to the present invention.
Figure 2:
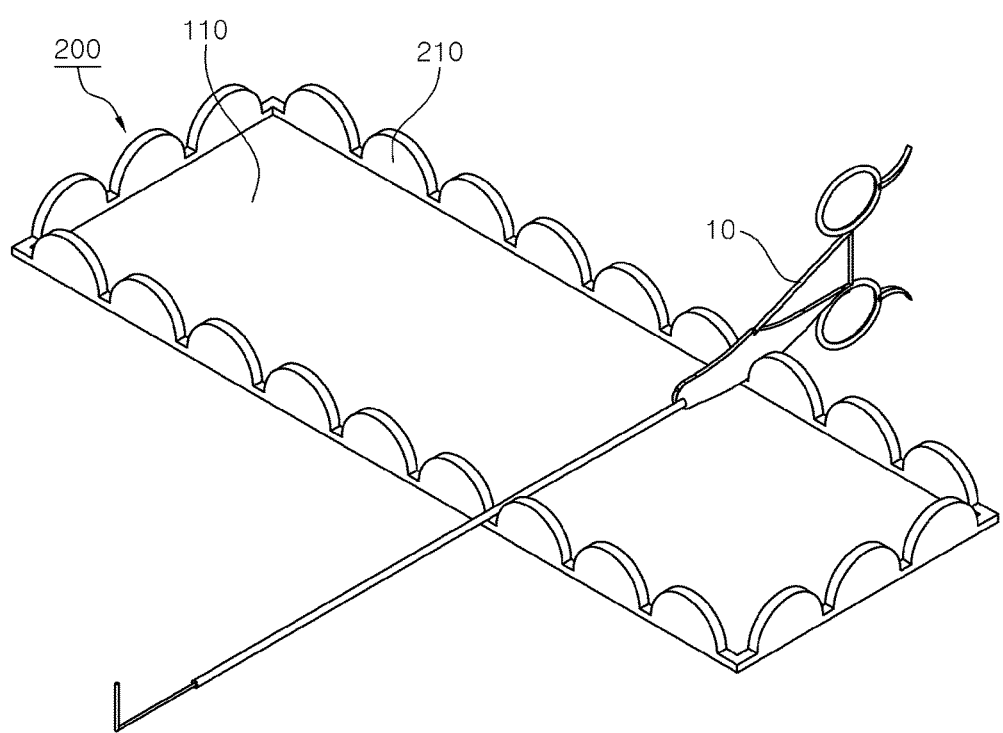
FIG. 2 shows a state in which surgical instruments are placed on the seating area of a soft pad.
Figure 3A:
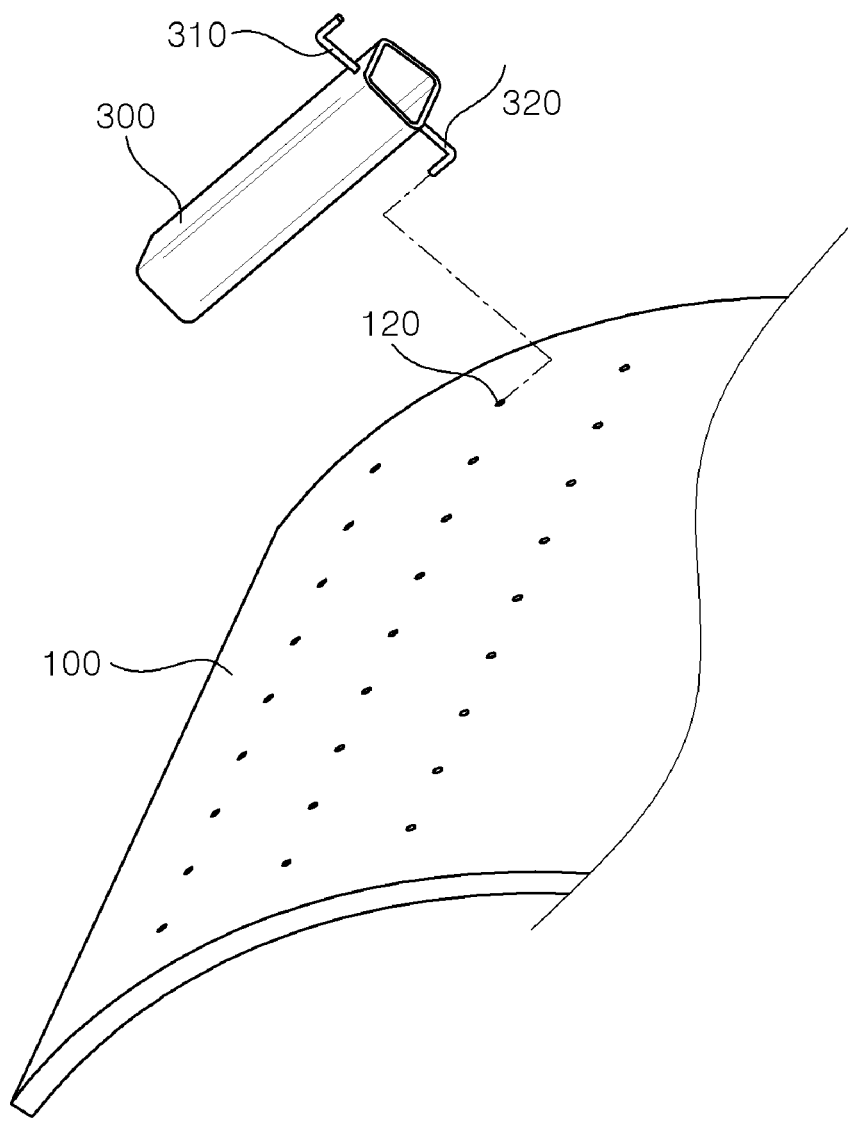
FIGS. 3A and 3B are perspective views showing a coupling structure for a detachable case and the soft pad included in the surgical instrument organizing pad according to the present invention.
Figure 3B:
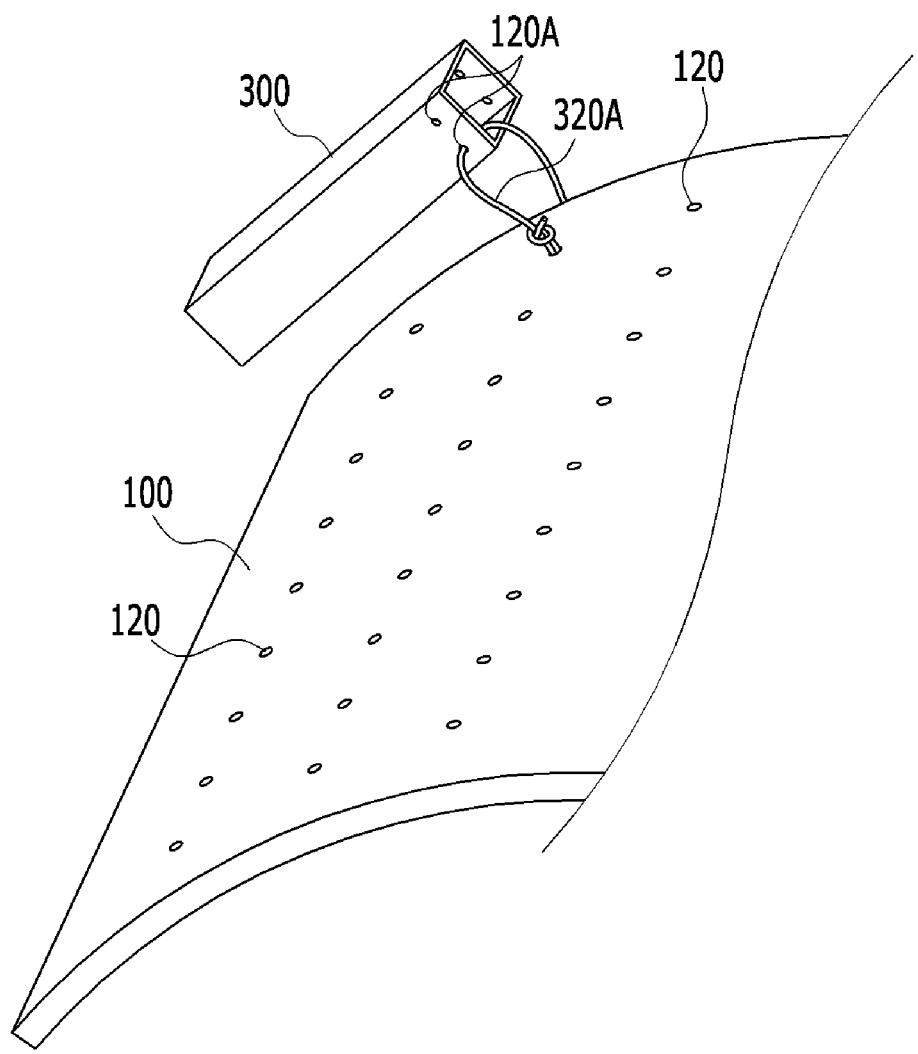

FIG. 1 is a perspective view of a surgical instrument organizing pad according to the present invention, FIG. 2 shows a state in which surgical instruments are placed on the seating area of a soft pad, and FIGS. 3A and 3B are exploded perspective views showing a coupling structure for a detachable case and the soft pad included in the surgical instrument organizing pad according to the present invention.

The surgical instrument organizing pad according to the present invention is a tool for stably placing various types of surgical instruments 10 to be used during surgery. The surgical instrument organizing pad is characterized in that the surgical instrument organizing pad can stably fasten even any types of surgical instruments 10 regardless of the material, size, dimensions, etc. of the surgical instruments 10.

In other words, the surgical instrument organizing pad according to the present invention is configured to include: a soft pad 100 configured such that it is fabricated in a size which enables it to be held on the body of a patient and a seating area 110 on which a surgical instrument 10 is seated is formed on the top surface of the center portion thereof; and partitions 200 erected along the circumference of the seating area 110.

The soft pad 100 and the partitions 200 are made of soft resin having considerably high frictional force. Even when a surgical instrument 10 seated on the soft pad 100 or partition 200 is inclined at a predetermined angle, it is prevented from sliding and falling easily. In other words, since the surgical instrument 10 placed on the surgical instrument organizing pad according to the present invention is fastened by frictional force, an advantage arises in that the surgical instrument 10 can be maintained in a considerably stably fastened state even when it is made of any material, such as stainless steel, titanium, or the like. In particular, in the case of a surgical instrument 10 having a small size so that it can enter into the seating area 110 surrounded by the partitions 200, an effect can be achieved in that it is prevented from falling out of the seating area 110 as long as the soft pad 100 is not completely turned upside down.

Alternatively, the soft pad 100 and the partitions may be made of fabric including cloth.

Furthermore, the surgical instrument organizing pad according to the present invention is made of a material harmless to a human body, and thus advantages arise in that the surgical instrument organizing pad does not cause injury to a patient or doctor and can be sterilized by heating, thereby being maintained in a sterile state.

Meanwhile, when the surgical instrument 10 is formed in an easily rotatable shape, i.e., a cylindrical shape, even when the surgical instrument organizing pad according to the present invention is made of soft resin having high frictional force, a problem arises in that the surgical instrument 10 is rotated and falls.

To overcome the above problem, the surgical instrument organizing pad according to the present invention is characterized in that each of the partitions 200 is configured to include a plurality of unit plates 210. When each of the partitions 200 is composed of the plurality of unit plates 210, rather than a single wall, as described above, a phenomenon in which the surgical instrument 10 is rotated and falls can be prevented by seating the surgical instrument 10 between two unit plates 210, as shown in FIG. 2.

In this case, when the diameter of the surgical instrument 10 is larger than the interval between the two unit plates 210, it is difficult to seat the surgical instrument 10 between the two unit plates 210. Accordingly, each of the unit plates 210 is preferably formed in a semicircular shape which is convex upward, as shown in the present embodiment. When each of the unit plates 210 is formed in a semicircular shape which is convex upward, as shown above, the surgical instrument 10 can be placed between the unit plates 210 even when it is formed in a thick cylindrical shape, and thus an advantage arises in that the surgical instrument 10 can be stably placed regardless of the dimensions of the surgical instrument 10.

Meanwhile, recently, the use of electrically operated surgical instruments 10 each provided with an electric cable 12 has increased. When the electric cable 12 is not fastened even when the electrically operated surgical instruments 10 is seated on the seating area 110, a problem arises in that it may fall down, for example, in the case where the electric cable 12 comes into the body of a user and is then pulled or shaken.

In the surgical instrument organizing pad according to the present invention, each pair of two neighboring ones of the unit plates 210 are preferably spaced apart from each other by an interval which enables the electric cable 12 of the surgical instrument 10 to pass between the two neighboring unit plates 210 so that the electric cable 12 of the surgical instrument 10 can pass between the two neighboring unit plates 210 and a space can be ensured to fasten a surgical instrument which is formed to be long and slender in accordance with endoscopic surgery corresponding to a current surgery trend. Furthermore, at least one clamp 130 configured to fasten the electric cable 12 of the surgical instrument 10 may be formed on the top surface of the soft pad 100.

When the surgical instrument organizing pad according to the present invention is configured as described above, the electric cable 12 of the surgical instruments 10 is fastened between two unit plates 210, and is fastened by the clamp 130 again. An advantage arises in that even the electrically operated surgical instrument 10 can be maintained in a considerably stably placed state.

Furthermore, when the number of surgical instruments 10 to be used in a surgery process is large, it is difficult to seat all the surgical instruments 10 on the seating area 110. Accordingly, a plurality of detachable cases 300 each configured to hold a surgical instrument 10 may be provided. The detachable cases 300 are formed in a box or pocket shape having an open top, and are detachably attached onto both sides of the soft pad 100 in the lengthwise direction thereof. An advantage arises in that a user may reduce or increase the number of detachable cases 300 depending on the type and number of surgical instruments 10 to be used for surgery. One or more detachable cases 300 may be further included. In this case, a hook 310 configured to hold the surgical instrument 10 may be provided on the outer surface of each of the detachable cases 300 so that the surgical instrument 10 can be hung on the detachable case 300 rather than being inserted into the detachable case 300.

When the detachable case 300 provided with the hook 310 is additionally included, as described above, a user may place the surgical instruments 10 at various locations according to his or her convenience, thereby enabling the individual surgical instruments 10 to be more conveniently used.

In this case, a plurality of mounting holes 120 may be formed in both sides of the soft pad 100 in the lengthwise direction thereof so that the detachable cases 300 can be detachably mounted onto the soft pad 100, and the detachable cases 300 may be provided with mounting tools 320 which can be inserted into the mounting holes 120. The mounting holes 120 may be uniformly distributed over the overall soft pad 100 so that the locations at which the detachable cases 300 are coupled can be freely changed according to a user's selection.

Furthermore, pluralities of mounting holes 120, 120A may be formed in both sides of the soft pad 100 in the lengthwise direction thereof and in the detachable cases 300. The mounting tools 320 may be replaced with mounting loops 320A which connect the mounting holes 120 formed in the soft pad 100 and the mounting holes 120A formed in the detachable cases 300.

Figure 4:
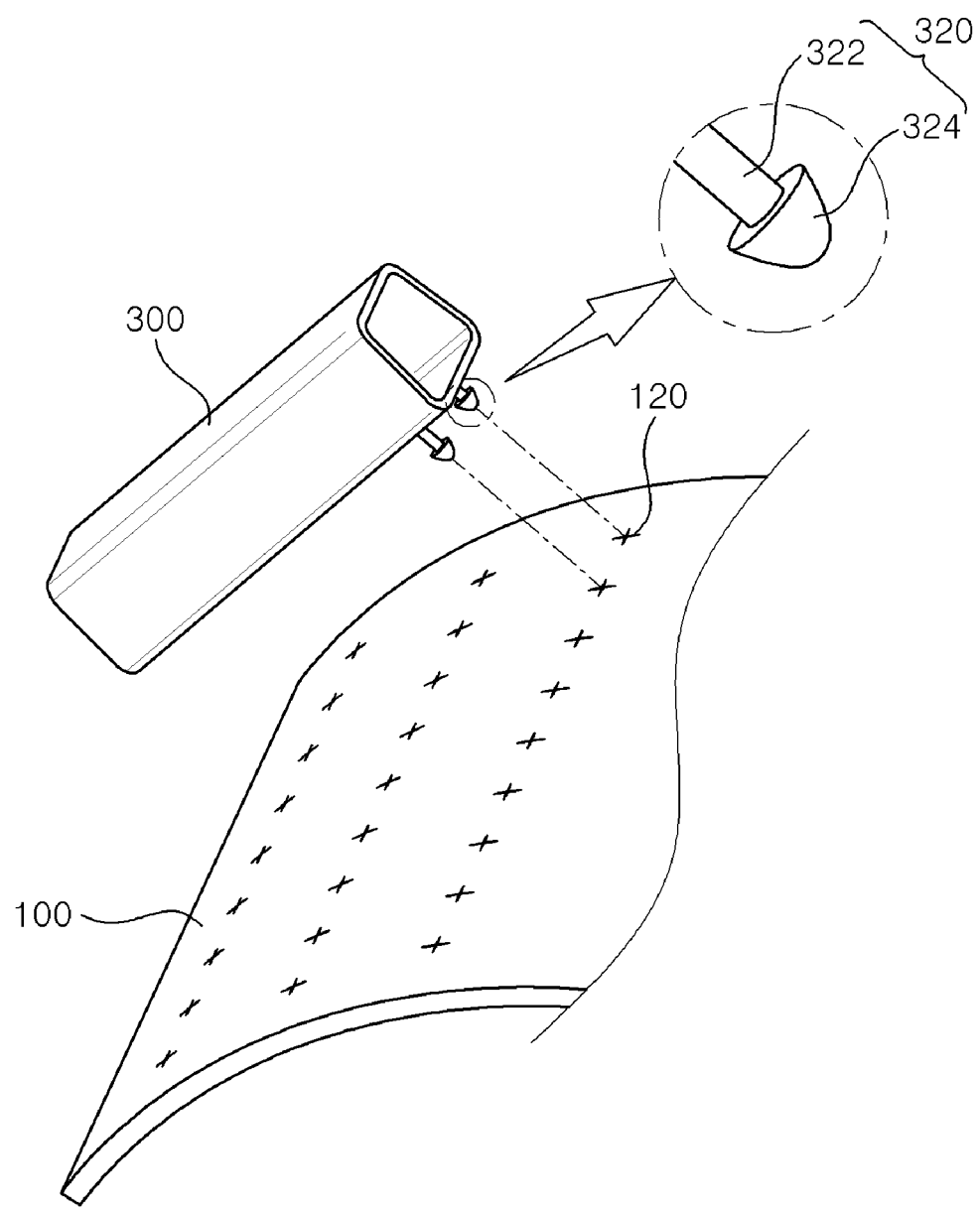
FIGS. 4 and 5 are an exploded perspective view and a sectional view showing a coupling structure for a detachable case and a soft pad included in a second embodiment of the surgical instrument organizing pad according to the present invention.
Figure 5:
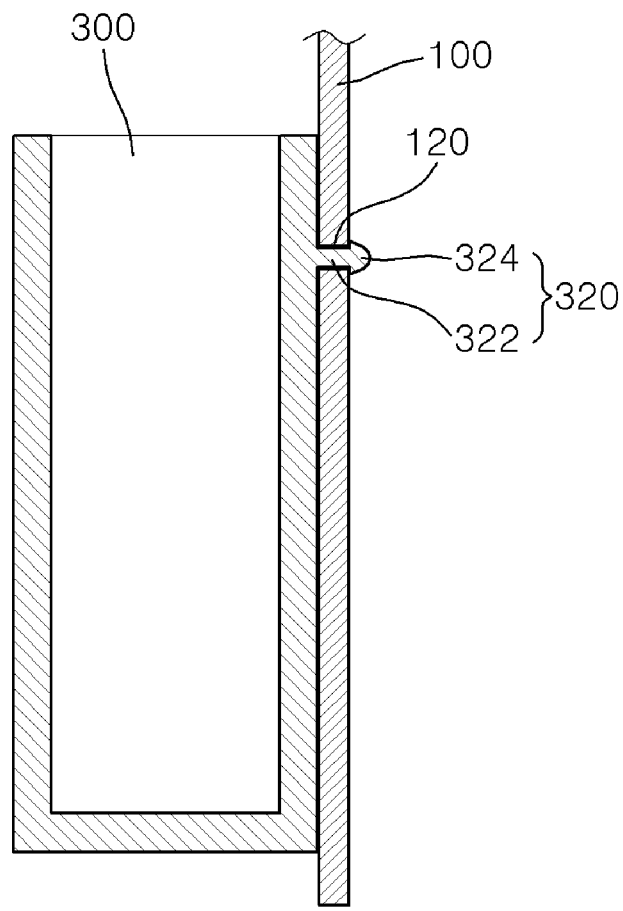

FIGS. 4 and 5 are an exploded perspective view and a sectional view showing a coupling structure for a detachable case 300 and a soft pad 100 included in a second embodiment of the surgical instrument organizing pad according to the present invention.

The detachable case 300 into which the surgical instrument 10 is inserted or on which the surgical instrument 10 is hung may be coupled to the soft pad 100 before the start of surgery. There may be required a case where the detachable case 300 needs to be added or a case where the location at which the detachable case 300 has been attached needs to be changed, during surgery.

In this case, when the mounting hole 120 and mounting tool 320 configured to couple the detachable case 300 into the soft pad 100 are formed in the shape of a circular through hole and in the shape of a bent pin, respectively, as in the embodiment shown in FIGS. 1 to 3A, the mounting tool 320 can be inserted into the mounting hole 120 only when an end of the mounting tool 320 is accurately aligned with the mounting hole 120. In this case, a disadvantage arises in that it is difficult to add the detachable case 300 and change the location at which the detachable case 300 has been coupled.

In order to overcome the above problem, i.e., in order to insert the mounting tool 320 into the mounting hole 120 even when the mounting tool 320 is not accurately aligned with the center of the mounting hole 120, the surgical instrument organizing pad according to the present invention may be configured such that the mounting hole 120 may be formed to be cut in a cross shape, as shown in the present embodiment. It will be apparent that as long as the mounting hole 120 can be inserted into the mounting tool 320, the mounting hole 120 may be formed in various shapes, such as a rectangular shape, etc. as well as a cross shape.

When the mounting hole 120 is formed in a cross shape, as described above, a user can insert the mounting tool 320 into the mounting hole 120 even when an end of the mounting tool 320 is not accurately aligned with the center of the mounting hole 120, and thus an advantage arises in that it may be possible to easily add the detachable case 300 and easily change the location at which the detachable case 300 has been coupled.

Meanwhile, in order to prevent the mounting tool 320 inserted into the mounting hole 120 from being easily separated therefrom, it is preferred that the mounting tool 320 is formed in the shape of a bent pin, as shown in FIG. 3A. When the mounting tool 320 is formed in the shape of a bent pin, as described above, it may be difficult to insert the mounting tool 320 into the mounting hole 120.

Accordingly, the mounting tool 320 included in the present invention is preferably configured such that the mounting tool 320 can be fully inserted into the mounting hole 120 through the manipulation of pushing the mounting tool 320 in one direction and the mounting tool 320 cannot be easily separated after being inserted into the mounting hole 120. In other words, the mounting tool 320 may include a stem portion 322 configured to protrude by the thickness of the soft pad 100 and a head portion 324 configured to have a sectional area larger than that of the stem portion 322 and decreasing toward an end thereof, as shown in FIG. 4 and FIG. 5.

When the mounting tool 320 includes the stem portion 322 and the head portion 324, as described above, the rear end of the head portion 324 comes into contact with the inner surface of the soft pad 100, as shown in FIG. 5, when the head portion 324 is inserted to fully pass through the mounting hole 120. In this case, the head portion 324 is not separated from the mounting hole 120 as long as the mounting hole 120 cut in a cross shape is not spread. Accordingly, an effect can be achieved in that the detachable case 300 coupled to the soft pad 100 is not separated from the soft pad 100 as long as large external force is not applied to the detachable case 300.

Figure 6:
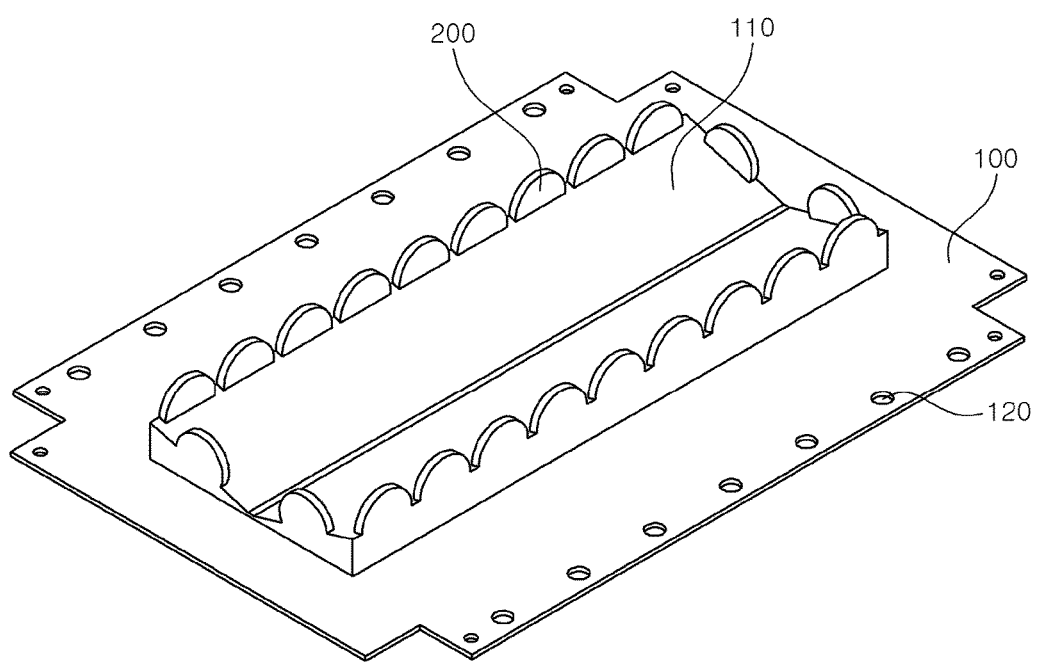
FIGS. 6 to 8 show another embodiment of the surgical instrument organizing pad according to the present invention.
Figure 7:
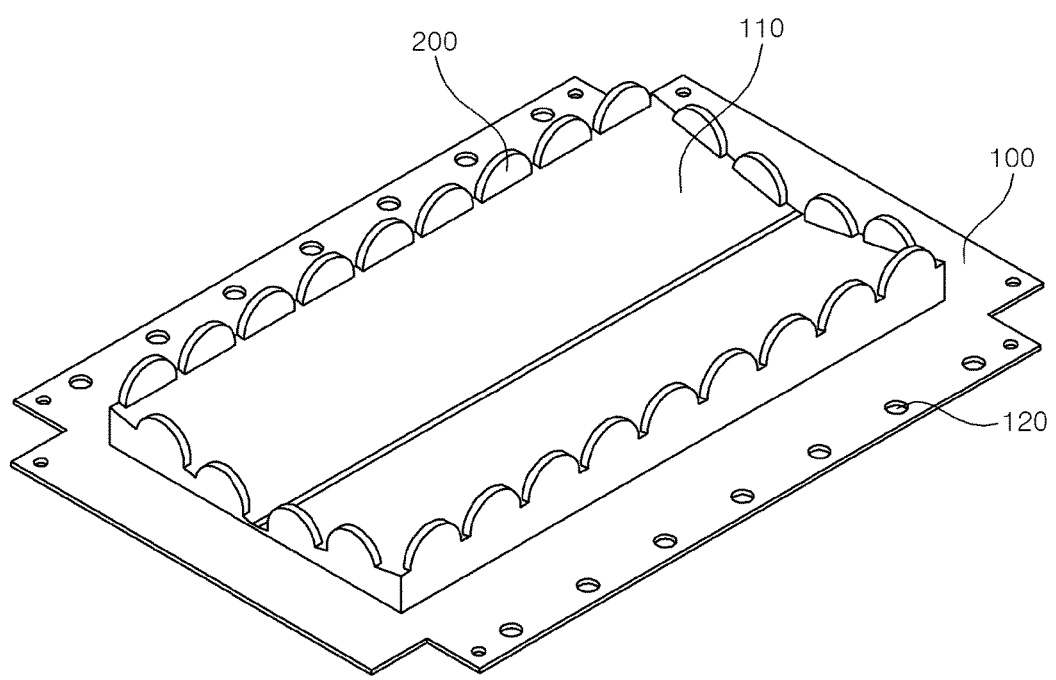
Figure 8:
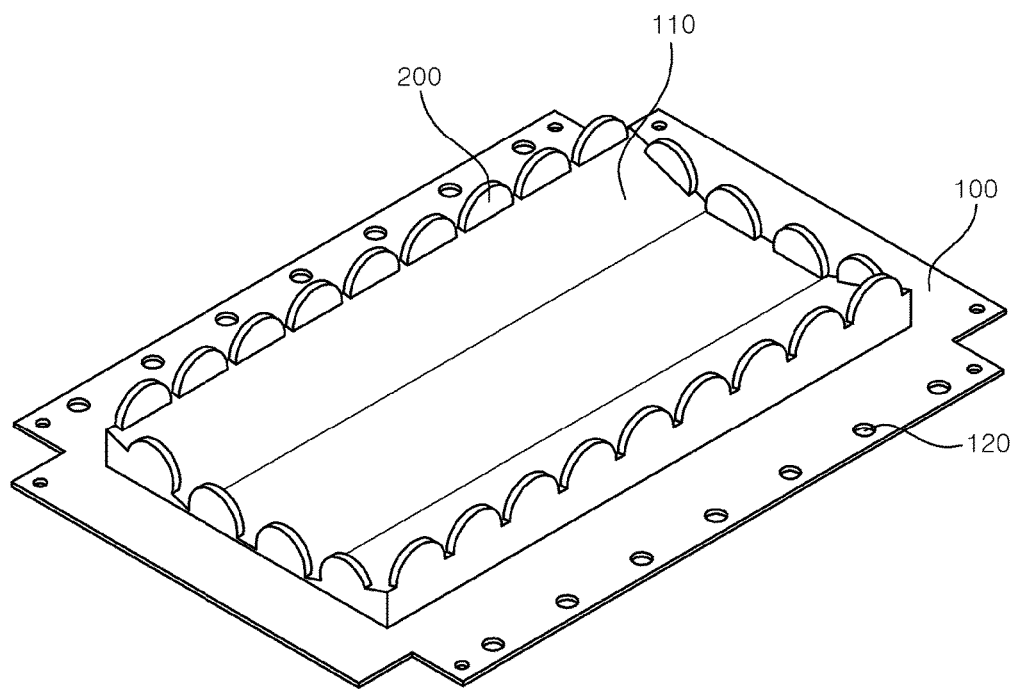

FIGS. 6 to 8 show another embodiment of the surgical instrument organizing pad according to the present invention.

When the surgical instrument organizing pad according to the present invention is seated on the abdomen or leg of a patient, the seating area 110 is deformed into an upward convex shape. In this case, it may be difficult to stably place a surgical instrument on the seating area 110. Accordingly, the seating area 110 may be formed to be inclined such that the height of the seating area 110 increases toward both ends of the seating area 110 in the widthwise direction thereof. In this case, the dimensions of the seating area 110 or the number of partitions 200 may be freely changed according to the usage or characteristic of the surgical instrument organizing pad.

Furthermore, when the soft pad 100 is fabricated in the shape of a rectangular plate, one or more corner portions of the soft pad 100 are separated from a support surface when the soft pad 100 is placed on the body of a patient, and thus a problem may arise in that the grip force of the soft pad 100 is deteriorated. Accordingly, the soft pad 100 included in the present invention may be fabricated in a shape which is chamfered in a rectangular shape at four corners, i.e., in a cross plate shape, as shown in FIGS. 6 and 7. In this case, the soft pad 100 may be fabricated in a cross shape having any dimensions as long as grip force can be improved.

Meanwhile, in the surgical instrument organizing pad according to the present invention, the shape of the seating area 110 may vary in various manners according to a sense of stability felt by a user and the characteristic of a bodily portion on which the soft pad 100 is seated. In other words, the seating area 110 may be formed to be inclined in a left-right direction so that the bottom surface thereof forms a "V" shape, as shown in FIGS. 6 and 7, or may be formed in a shape in which inclined surfaces are provided on left and right sides and a flat surface is provided at a center portion, as shown in FIG. 8. It will be apparent that the bottom surface shape of the seating area 110 may be formed in various shapes, in addition to the shape shown in the present embodiment.

While the present invention has been described in detail by using the preferred embodiments, the scope of the present invention is not limited to specific embodiments, and should be constructed based on the attached claims. Furthermore, it will be apparent to those having ordinary knowledge in the art that many modifications and alterations can be made without departing from the scope of the present invention.

DESCRIPTION OF REFERENCE SYMBOLS

10: surgical instruments
12: electric cable
100: soft pad
110: seating area
120: mounting hole
130: clamp
200: partition
210: unit plate
300: detachable case
310: hook
320: mounting tool
322: stem portion
324: head portion

The invention claimed is:

1. A surgical instrument organizing pad comprising:
a soft pad configured such that it is fabricated in a size which enables the pad to be held on a body of a patient and a seating area on which surgical instruments are seated is formed on a top surface of a center portion thereof; and
partitions erected along a circumference of the seating area;
wherein the soft pad and the partitions are made of soft resin, and
wherein each of the partitions includes a plurality of unit plates, each pair of two neighboring ones of the unit plates are spaced apart from each other by a predetermined distance, and each of the unit plates is formed in an upward convex shape along the circumference of the seating area such that a space between the two neighboring unit plates is increased along an upward vertical direction so as to fasten the surgical instruments of various sizes.

2. The surgical instrument organizing pad of claim 1, further comprising:
one or more detachable cases formed in a box or pocket shape having an open top, and configured to be detachably attached onto two sides of the soft pad in a lengthwise direction thereof.

3. The surgical instrument organizing pad of claim 2, wherein:
a plurality of mounting holes are formed in both sides of the soft pad in the lengthwise direction thereof; and
the one or more detachable cases are provided with mounting tools which can be inserted into the mounting holes.

4. The surgical instrument organizing pad of claim 2, wherein pluralities of mounting holes are formed in both sides of the soft pad in the lengthwise direction thereof and in the one or more detachable cases;
further comprising mounting loops configured to connect the mounting holes of the soft pad and the mounting holes of the one or more detachable cases.

5. The surgical instrument organizing pad of claim 1, wherein:
the soft pad is formed in a cross or rectangular shape on a plane; and
the seating area is formed to be inclined such that a height of the seating area increases toward both ends of the seating area in a widthwise direction thereof.

* * * * *